United States Patent
Dubey et al.

(10) Patent No.: US 12,378,180 B2
(45) Date of Patent: Aug. 5, 2025

(54) RECYCLABLE AND REWORKABLE POLYOL(S)

(71) Applicant: Aditya Birla Chemicals (Thailand) Ltd. (Epoxy Division), Khet Pathumwan Bankgkok (TH)

(72) Inventors: Pradip Kumar Dubey, Andheri (east) Mumbai (IN); Chandan Kumar Singh, Muang Rayong (TH); Kanyarat Sittipummongkol, Muang Rayong (TH); Weerawat Sripet, Muang Rayong (TH)

(73) Assignee: Aditya Birla Chemicals (Thailand) Ltd. (Epoxy Division), Bangkok (TH)

( * ) Notice: Subject to any disclaimer, the term of this patent is extended or adjusted under 35 U.S.C. 154(b) by 735 days.

(21) Appl. No.: 17/621,793

(22) PCT Filed: May 19, 2020

(86) PCT No.: PCT/IB2020/054717
§ 371 (c)(1),
(2) Date: Dec. 22, 2021

(87) PCT Pub. No.: WO2020/260970
PCT Pub. Date: Dec. 30, 2020

(65) Prior Publication Data
US 2022/0267240 A1 Aug. 25, 2022

(30) Foreign Application Priority Data

Jun. 27, 2019 (IN) .............................. 201911025647

(51) Int. Cl.
| | |
|---|---|
| *C08G 18/32* | (2006.01) |
| *C07C 43/315* | (2006.01) |
| *C07C 69/94* | (2006.01) |
| *C07F 7/08* | (2006.01) |
| *C07F 7/18* | (2006.01) |
| *C08G 18/38* | (2006.01) |
| *C08G 18/76* | (2006.01) |
| *C08G 18/82* | (2006.01) |
| *C08J 11/18* | (2006.01) |

(52) U.S. Cl.
CPC ............ *C07C 43/315* (2013.01); *C07C 69/94* (2013.01); *C07F 7/0834* (2013.01); *C07F 7/1804* (2013.01); *C08G 18/3206* (2013.01); *C08G 18/3215* (2013.01); *C08G 18/3893* (2013.01); *C08G 18/7671* (2013.01); *C08G 18/82* (2013.01); *C08J 11/18* (2013.01); *C08J 2375/04* (2013.01)

(58) Field of Classification Search
USPC .......................................................... 521/49
See application file for complete search history.

(56) References Cited

U.S. PATENT DOCUMENTS

| | | | | |
|---|---|---|---|---|
| 2,945,008 A | * | 7/1960 | Caldwell ................ | C08G 63/66 528/196 |
| 3,424,726 A | * | 1/1969 | Schade ................ | C07D 319/06 528/307 |
| 5,917,059 A | | 6/1999 | Bruchmann et al. | |
| 6,187,893 B1 | | 2/2001 | Bruchmann et al. | |

FOREIGN PATENT DOCUMENTS

| | | | | |
|---|---|---|---|---|
| EP | 1894957 A1 | * | 3/2008 | ............... B41C 1/05 |
| JP | 2005307083 A | | 11/2005 | |
| WO | WO-2015081610 A1 | * | 6/2015 | ............... B32B 5/26 |

OTHER PUBLICATIONS

Reaxys: "REAXYS Result of Online Query: OH-functional acetals, ketals and orthoesters", 2020.
Nguyen Thi Thuy et al., Synthesis of bio-polyols by epoxide ring opening reaction with H2O as a reagent, Vietnam Journal of Chemistry, International Edition, pp. 411-416, 2017.
Myriam Desroches et al., From Vegetable Oils to Polyurethanes: Synthetic Routes to Polyols and Main Industrial Products, Jan. 2012.
Pathiraja A. Gunatillake et al., Biodegradable Polyurethanes: Design, Synthesis, Properties and Potential Applications, Jan. 2011.
John O. Akindoyo et al., Polyurethane types, synthesis and applications—a review, The Royal Society of Chemistry, 2016.
PCT Office, Search Report and Written Opinion issued in PCT/IB2020/054717 mailed on Sep. 21, 2020.

* cited by examiner

*Primary Examiner* — Terressa Boykin
(74) *Attorney, Agent, or Firm* — Wood Herron & Evans LLP

(57) ABSTRACT

Polyol component(s) for a recyclable polyurethane system is disclosed. The recyclable polyurethane system comprises a polyol component having a structural Formula (I), a polyol component having a structural Formula (II) or a polyol component having a structural Formula III and an isocyanate curing agent. A process(es) for preparing the polyol component having the structural Formula (I), the polyol component having the structural Formula (II) and the polyol component having the structural Formula (III) is also disclosed.

8 Claims, No Drawings

RECYCLABLE AND REWORKABLE POLYOL(S)

FIELD OF THE INVENTION

The present disclosure relates to polyol(s) and a process for production of the polyol(s). Specifically, the disclosure relates to recyclable and reworkable polyol(s) for a polyurethane system.

BACKGROUND

Polyurethanes (PUs) are class of thermoset materials used extensively in diverse applications like rigid foam insulation panels, high strength flexible foams, microcellular foam seal and gaskets, high strength elastomeric wheels and tires, electronics instruments, hard plastics, automotive bushings and household things. PUs offers unique properties such as excellent abrasion resistance, high resilience, good electrical properties, excellent adhesions, low temperature flexibility and high strength make PUs an ideal choice for electrical potting and encapsulations.

Currently, PUs are one of the most common, versatile and researched materials in the world. They have been widely used in biomedical applications, building and construction applications, automotive, textiles and in several other industries due to their superior properties in terms of hardness, elongation, strength and modulus. PUs composites are one of the growing areas due to fast curing, automatable and superior quality. With more convenience in processing know-how and reactivity control to extend working time PUs has become an alternate for composite applications mainly dominated by unsaturated polyesters and vinyl esters. PUs composites are primarily used in foamed structural reaction injection molding (SRIM), automotive interiors, load floors, door panels and package shelves. PUs composites can be produced using pultrusion, filament windings and vacuum infusion techniques. Collectively, these applications make up to 5% of total composite market. However, similar to epoxy and polyester composites, PUs composites also are non-reworkable and non-recyclable. These limitations cause higher costs of the PUs composites and end of life disposal issues.

To date, several recycling methods have been brought forward for recycling of PUs polymer such as physical recycling, thermal recycling or chemical recycling. Physical recycling is done by crushing and breaking the PUs polymer into small pieces and using these pieces as filler, compression moulding and other lesser value applications. Thermal recycling involves incinerating the PUs to a very high temperature and high pressure. Chemical recycling utilizes high temperatures, special solvents, special processing and/or metal catalysts for recycling/reprocessing of PUs. However, these treatments have a significant limitation such as global warming, release of toxic gases, ash land filling and damage to the environment. Additionally, these methods are expensive, uneconomical and inefficient and industrially not feasible.

SUMMARY OF THE INVENTION

The present disclosure relates to a polyol component (s) for a recyclable polyurethane system, the polyol component having a structural Formula (I) or a structural Formula (II) or a structural Formula (III):

(Formula I)

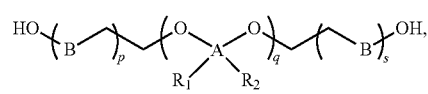

(Formula II)

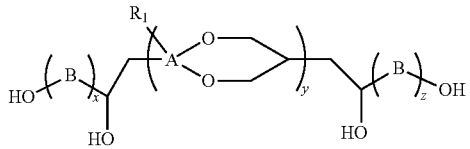

(Formula III)

wherein
m=0 then n=4,
m=1 then n=3,
m=2 then n=2,
A is carbon or silicon,
p, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.
B is independently selected from a group of arylene, arylene ethers, alkylene-arylene, alkylene-arylene, alkylene, alkenylene-arylene, alkenylene-arylene alkenylene, and alkylene-arylene-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

A process for preparing a polyol component having a structural Formula (I) and a polyol component having a structural Formula (II) for a polyurethane system is also disclosed. The process comprises reacting a compound having a structural Formula (IV) or a compound having a structural Formula (V) with water in the presence of a base at an elevated temperature to obtain a reaction mixture comprising the polyol component having the structural Formula (I) or a reaction mixture comprising the polyol component having the structural Formula (II), wherein the compound having the structural Formula (IV) and the compound having the structural Formula (V) is represented by:

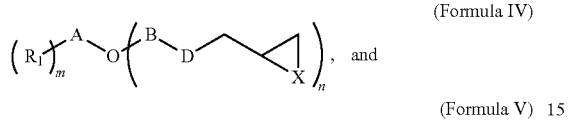
(Formula IV)

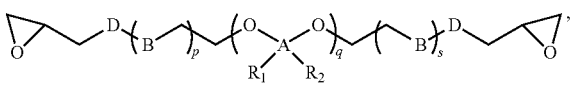
(Formula V)

wherein
m=0 then n=4,
m=1 then n=3,
m=2 then n=2,
A is carbon or silicon
D is oxygen or nitrogen or carboxylic group,
X is oxygen,
p, q, and s is independently from 1 to 20,
$R_1$ is selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.
B is selected from a group of arylene, alkylene-arylene, alkylene-arylene alkylene, alkenylene-arylene, alkenylene-arylene alkenylene, alkylene-arylene-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene, wherein the polyol component having the structural Formula (I) and the polyol component having the structural Formula (II) is:

(Formula I)

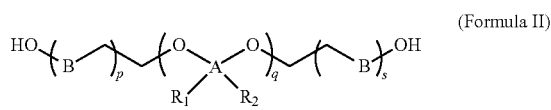
(Formula II)

wherein
m=0 then n=4,
m=1 then n=3,
m=2 then n=2,
A is carbon or silicon,
p, q, and s is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

An alternate process of preparing a polyol component having a structural Formula (I), a polyol component having a structural Formula (II) and a polyol component having the structural Formula (III) for a polyurethane system is also disclosed. The process comprises reacting a polyhydroxy compound having a structural Formula (VI) with a compound having a structural Formula (VII) or a compound having a structural Formula (VIII) or a compound having a structural Formula (IX) in the presence of an acidic catalyst to obtain the polyol component having the structural Formula (I), the polyol component having the structural Formula (II) and the polyol component having the structural Formula (III), wherein the compound having the structural Formula (VI) is represented by:

(Formula IV)

$$HO-\underset{R_2}{\underset{|}{C}}(R_1)-\underset{OH}{\underset{|}{C}}(R_2)_w-OH$$

wherein
w is 0 to 20
$R_1$, $R_2$, and $R_3$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, the compound having the structural Formula (VII) is represented by:

(Formula VII)

$$R_1-\underset{\parallel}{\overset{O}{C}}-R_2$$

wherein
$R_1$ and $R_2$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy;

the compound having the structural Formula VIII is represented by:

(Formula VIII)

$$R_3-\underset{R_4}{\overset{R_2}{\underset{|}{\overset{|}{C}}}}-O-R_1,$$

wherein
$R_1$ is independently selected from a group of hydrogen, alkyl, aryl, aralkyl, alkenyl, or alkynyl,
$R_2$, $R_3$, and $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, the compound having the structural Formula (IX) is represented by:

(Formula IX)

$$R_3-\underset{R_4}{\overset{R_1}{\underset{|}{\overset{|}{Si}}}}-R_2;$$

wherein
$R_1$, $R_2$, $R_3$, and $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, wherein
the polyol component having the structural Formula (I), the polyol component having the structural Formula (II) and the polyol component having the structural Formula (III) is:

(Formula I)

$$[R1\!\!\leftarrow\!\!\!\!\!]_m\!\!-\!\!A\!\!\leftarrow\!\!O\!-\!\!B\!-\!\!OH]_n,$$

(Formula II)

$$HO\!\leftarrow\!B\!\!\!\!\!]_p\!\!\!\!\left(\!\!\!\overset{O}{\underset{R_1}{\overset{|}{A}}}\!\!\!\overset{O}{\underset{R_2}{}}\!\!\!\right)_{\!\!q}\!\!\!\!\leftarrow\!B\!\!\!\!\!]_s\!\!OH,$$

(Formula III)

$$HO\!\leftarrow\!B\!\!\!\!\!]_x\!\!\!\left(\!\!\!\!\underset{HO}{\overset{R_1}{\underset{|}{\overset{O}{A}}}}\!\!\!\!\overset{O}{\underset{}{}}\!\!\!\right)_{\!\!y}\!\!\!\!\leftarrow\!B\!\!\!\!\!]_z\!\!OH$$

wherein
m=0 then n=4,
m=1 then n=3,
m=2 then n=2,
A is carbon or silicon,
P, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

The present disclosure also concerns a recyclable polyurethane system. A recyclable polyurethane system comprising a reaction product made by reacting an isocyanate curing agent with a polyol component having a structural Formula (I), or a polyol component having a structural Formula (II) or a polyol component having a structural Formula (III); wherein the polyol component having the structural Formula (I) or the polyol component having the structural Formula (II) or the polyol having the structural Formula (III) is represented by:

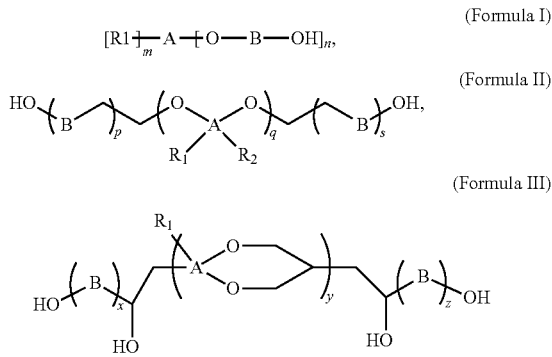

wherein
m=0 then n=4,
m=1 then n=3,
m=2 then n=2,
A is carbon or silicon,
P, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

The present disclosure further concerns a process for recycling a polyurethane system. The process comprises heating the polyurethane system and immersing the heated polyurethane system in an acid and a solvent at a temperature in a range of 80 to 220° C. The recyclable polyurethane system being a reaction product of a polyol component having a structural Formula (I) or a polyol component having a structural Formula (II) or a polyol component having a structural Formula (III) and an isocyanate curing agent.

DETAILED DESCRIPTION OF THE INVENTION

For the purpose of promoting an understanding of the principles of the invention, reference will now be made to embodiments and specific language will be used to describe the same. It will nevertheless be understood that no limitation of the scope of the invention is thereby intended, such alterations and further modifications in the disclosed process, and such further applications of the principles of the invention therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "one embodiment" "an embodiment" or similar language means that a particular feature, structure, or characteristic described in connection with the embodiment is included in at least one embodiment of the present invention. Thus, appearances of the phrase "in one embodiment", "in an embodiment" and similar language throughout this specification may, but do not necessarily, all refer to the same embodiment.

In one aspect, the present disclosure provides a polyol component(s) for a polyurethane system. Specifically, the present disclosure provides the polyol component(s) for a recyclable polyurethane system.

The term "recyclable polyurethane system" in context of the present disclosure means a system which is capable of softening in the mixture of an acid and a solvent at elevated temperature, which result in the dissolution of the polyol component (s) of the polyurethane system. The polyol component (s) is capable of dissolution in these conditions because the cross-links in the polyurethane matrix is acid labile and undergo a bond cleavage reaction.

The polyol component (s) for the recyclable polyurethane system has a structural Formula (I) or a structural Formula (II) or a structural Formula (III).

In accordance with an embodiment, the polyol component having the structural Formula (I) is represented by:

wherein
m=0 then n=4,
m=1 then n=3,
m=2 then n=2,
A is carbon or silicon,
$R_1$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl;
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

In accordance with an embodiment, B can be same or different substituent groups.

In accordance with an embodiment, the polyol component having the structural Formula (I), is one of the following compounds:

TABLE 1

Compounds of Structural Formula (I)

| S. No. | Compounds of structural Formula I |
|---|---|
| P-1 | 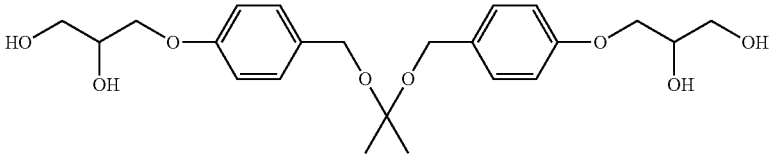 [SMILES: CC(C)(OCc1ccc(OCC(O)CO)cc1)OCc1ccc(OCC(O)CO)cc1] |
| P-2 | 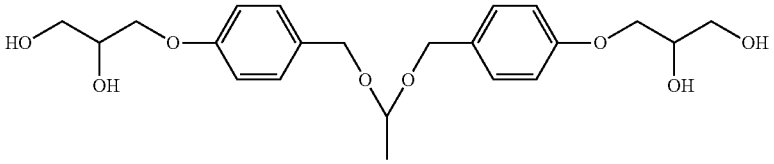 [SMILES: CC(OCc1ccc(OCC(O)CO)cc1)OCc1ccc(OCC(O)CO)cc1] |
| P-3 | 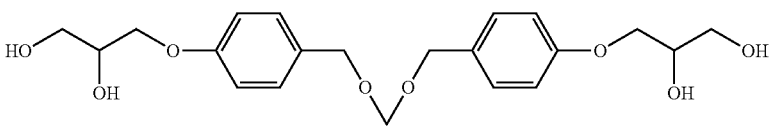 [SMILES: OCC(O)COc1ccc(COCOCc2ccc(OCC(O)CO)cc2)cc1] |
| P-4 | 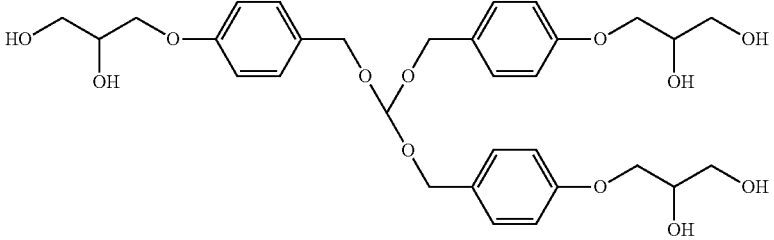 [SMILES: OCC(O)COc1ccc(COC(OCc2ccc(OCC(O)CO)cc2)OCc2ccc(OCC(O)CO)cc2)cc1] |

TABLE 1-continued
Compounds of Structural Formula (I)
| S. No. | Compounds of structural Formula I |
|---|---|
| P-5 | 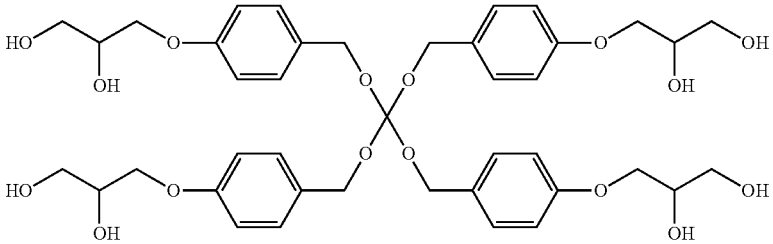 [SMILES: OCC(O)COc1ccc(COC(OCc2ccc(OCC(O)CO)cc2)(OCc2ccc(OCC(O)CO)cc2)OCc2ccc(OCC(O)CO)cc2)cc1] |
| P-6 | 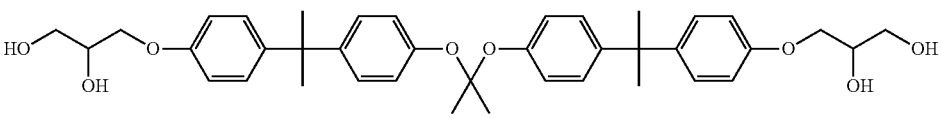 [SMILES: CC(C)(Oc1ccc(C(C)(C)c2ccc(OCC(O)CO)cc2)cc1)Oc1ccc(C(C)(C)c2ccc(OCC(O)CO)cc2)cc1] |
| P-7 | 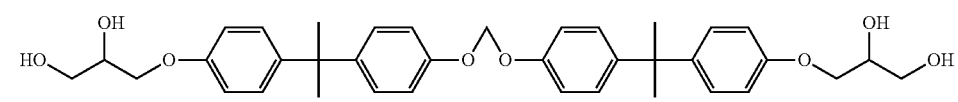 |
| P-8 | 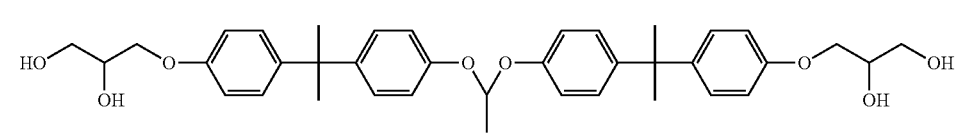 [SMILES: CC(Oc1ccc(C(C)(C)c2ccc(OCC(O)CO)cc2)cc1)Oc1ccc(C(C)(C)c2ccc(OCC(O)CO)cc2)cc1] |
| P-9 | 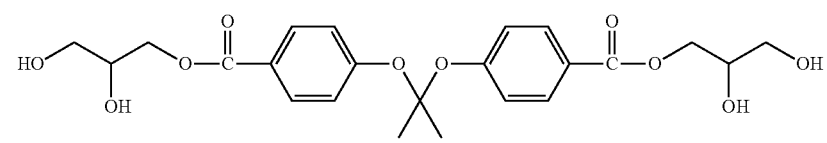 [SMILES: CC(C)(Oc1ccc(C(=O)OCC(O)CO)cc1)Oc1ccc(C(=O)OCC(O)CO)cc1] |
| P-10 | 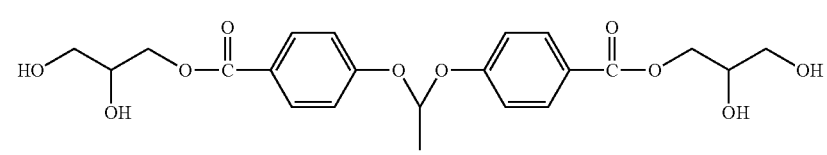 [SMILES: CC(Oc1ccc(C(=O)OCC(O)CO)cc1)Oc1ccc(C(=O)OCC(O)CO)cc1] |
| P-11 | 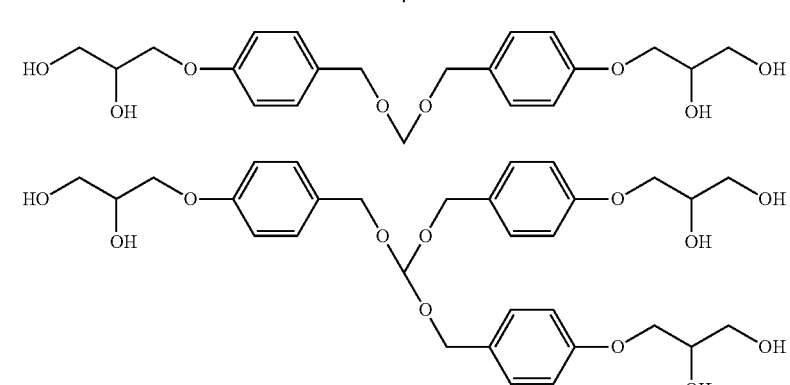 |
| P-12 | 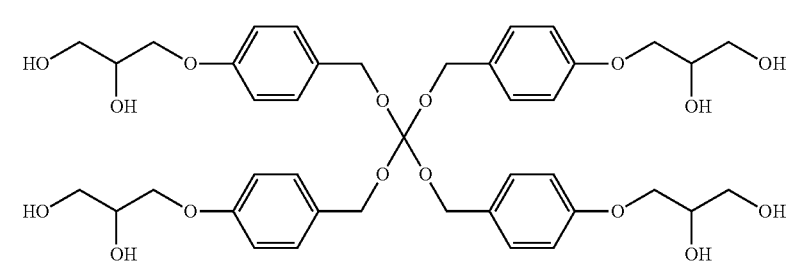 [SMILES: OCC(O)COc1ccc(COC(OCc2ccc(OCC(O)CO)cc2)(OCc2ccc(OCC(O)CO)cc2)OCc2ccc(OCC(O)CO)cc2)cc1] |

TABLE 1-continued
| Compounds of Structural Formula (I) | |
|---|---|
| S. No. | Compounds of structural Formula I |
| P-13 | 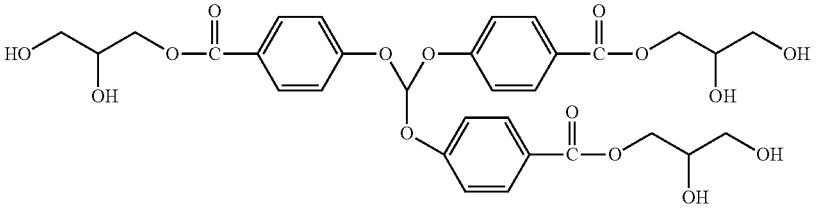 [SMILES: O=C(OCC(O)CO)c1ccc(OC(Oc2ccc(C(=O)OCC(O)CO)cc2)Oc2ccc(C(=O)OCC(O)CO)cc2)cc1] |
| P-14 | 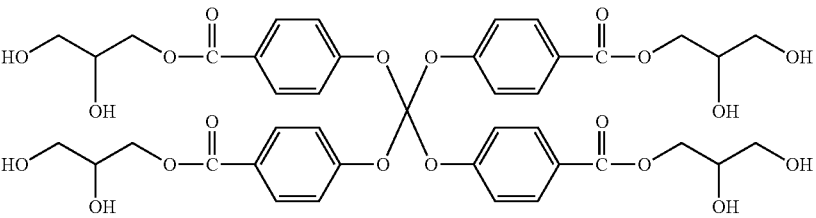 [SMILES: O=C(OCC(O)CO)c1ccc(OC(Oc2ccc(C(=O)OCC(O)CO)cc2)(Oc2ccc(C(=O)OCC(O)CO)cc2)Oc2ccc(C(=O)OCC(O)CO)cc2)cc1] |
| P-15 | 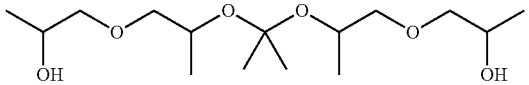 [SMILES: CC(O)COCC(C)OC(C)(C)OC(C)COCC(C)O] |
| P-16 |  |
| P-17 | 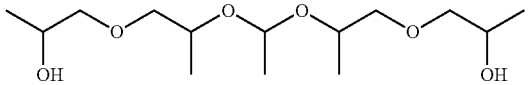 [SMILES: CC(O)COCC(C)OC(C)OC(C)COCC(C)O] |
| P-18 | 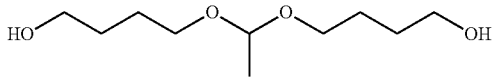 |
| P-19 | 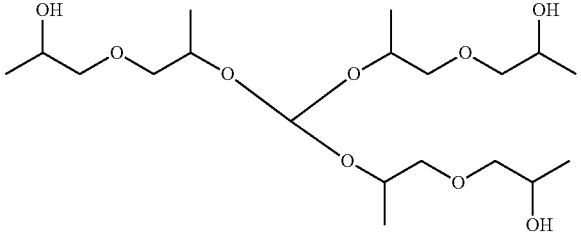 [SMILES: CC(O)COCC(C)OC(OC(C)COCC(C)O)OC(C)COCC(C)O] |
| P-20 | 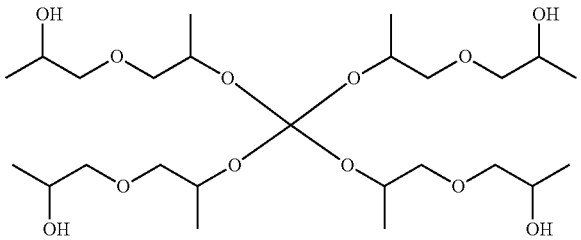 [SMILES: CC(O)COCC(C)OC(OC(C)COCC(C)O)(OC(C)COCC(C)O)OC(C)COCC(C)O] |
| P-21 | 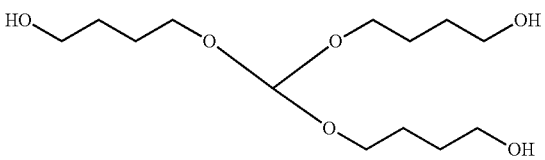 [SMILES: OCCCCOC(OCCCCO)OCCCCO] |

TABLE 1-continued
Compounds of Structural Formula (I)
| S. No. | Compounds of structural Formula I |
|---|---|
| P-22 | 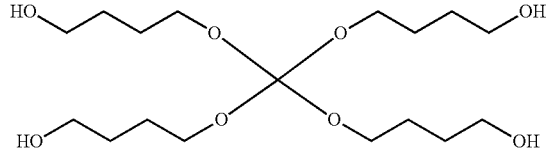 [SMILES: OCCCCOC(OCCCCO)(OCCCCO)OCCCCO] |
| P-23 | 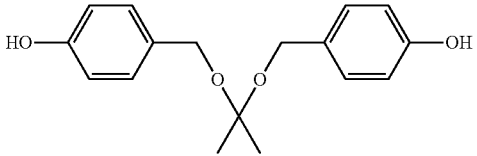 [SMILES: CC(C)(OCc1ccc(O)cc1)OCc1ccc(O)cc1] |
| P-24 | 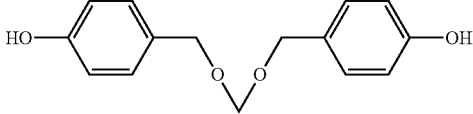 [SMILES: Oc1ccc(COCOCc2ccc(O)cc2)cc1] |
| P-25 | 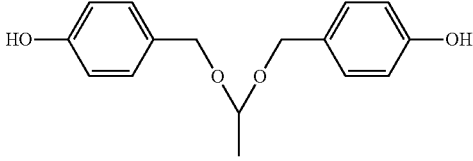 [SMILES: CC(OCc1ccc(O)cc1)OCc1ccc(O)cc1] |
| P-26 | 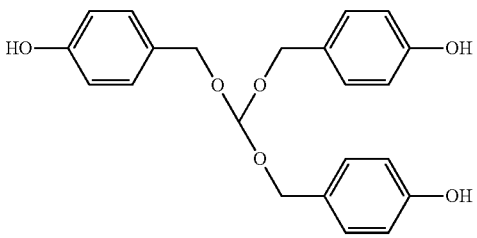 [SMILES: Oc1ccc(COC(OCc2ccc(O)cc2)OCc2ccc(O)cc2)cc1] |
| P-27 | 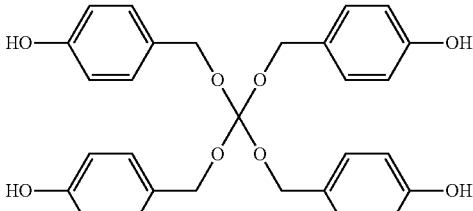 |
| P-28 | 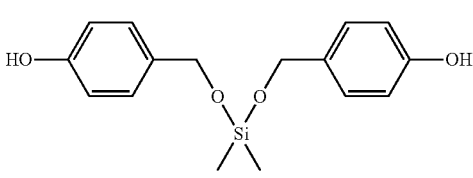 [SMILES: C[Si](C)(OCc1ccc(O)cc1)OCc1ccc(O)cc1] |
| P-29 | 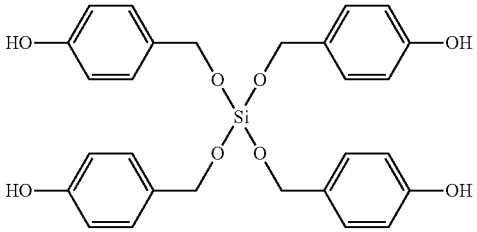 [SMILES: Oc1ccc(CO[Si](OCc2ccc(O)cc2)(OCc2ccc(O)cc2)OCc2ccc(O)cc2)cc1] |

TABLE 1-continued

Compounds of Structural Formula (I)

| S. No. | Compounds of structural Formula I |
|---|---|
| P-30 | 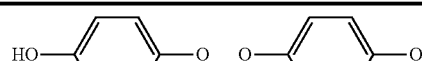 |
| P-31 | 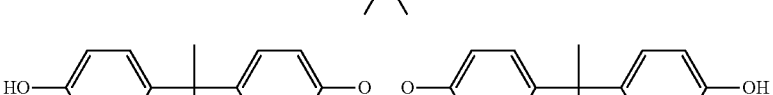 |

In accordance with an embodiment, the polyol component having the structural Formula (II) is represented by:

(Formula II)

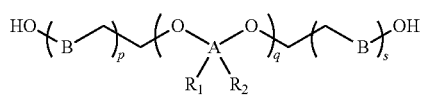

wherein

A is carbon or silicon, p, q, and s is independently from 1 to 20, $R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.

B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

In accordance with an embodiment, B can be same or different substituent groups.

In accordance with an embodiment, the polyol component having the structural Formula (II) is one of the following compounds:

TABLE 2

Compounds of structural Formula (II)

| S. No. | Compounds of Structural Formula (II) |
|---|---|
| PP-1 | 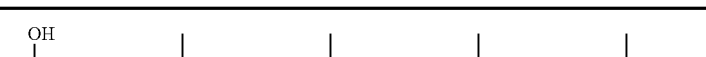 |
| PP-2 | 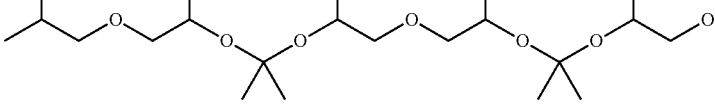 |

TABLE 2-continued

Compounds of structural Formula (II)

| S. No. | Compounds of Structural Formula (II) |
|---|---|
| PP-3 | (structure) |
| PP-4 | (structure) |
| PP-5 | (structure) |
| PP-7 | (structure) |
| PP-8 | (structure) |
| PP-9 | (structure) |
| PP-10 | (structure) |
| PP-11 | (structure) |

In accordance with an embodiment, the polyol component having the structural Formula (III) is represented by:

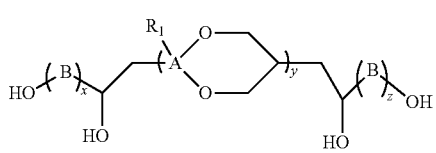

wherein
x, y and z is independently from 1 to 20,
R$_1$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.
B is independently arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

In accordance with an embodiment, B can be same or different substituent groups.

In accordance with an embodiment, the polyol component having the structural Formula (III) is one of the following compounds:

TABLE 3

Compounds of structural Formula (III)

| S. No. | Compounds of Structural Formula (III) |
|---|---|
| PPP-1 | |
| PPP-2 | |
| PPP-3 | |
| PPP-4 | |
| PPP-5 | |

In accordance with an embodiment, the polyol component having the structural Formula (I), the polyol component having the structural Formula (II) and the polyol component having the structural Formula (III) includes at least one cleavage point. The cleavage point is either a formal functional group, an acetal functional group, a ketal functional group, an orthoester functional group and an orthocarbonate functional group. The formal functional group, acetal functional group, ketal functional group, orthoester functional group and orthocarbonate functional group of the polyol component (s) are degradable upon exposure to elevated temperature or an acidic medium. Thus, the softening of the polyol component having the structural Formula (I), the polyol component having the structural Formula (II) and the polyol component having the structural Formula (III) is as a result of the decomposition of the formal functional group, acetal functional group, ketal functional group, orthocarbonate functional group and orthoester functional group in the polyol component(s) and which allows the PUs to be recyclable.

In accordance with an embodiment, the polyol component having the structural Formula (I) has a number average molecular weight (Mn) of 100 to 1000, the polyol component having the structural Formula (II) has a number average molecular weight of 200 to 1500 and the polyol component having the structural Formula (III) has a number average molecular weight (Mn) of 100 to 1200.

In accordance with an embodiment, the viscosity of the polyol component having the structural Formula (I) is in a range of 50 mPa·s to 20,000 mPa·s. The viscosity of the polyol component having the structural Formula (II) and the polyol component having the structural Formula (III) is in a range of 200 mPa·s to 60,000 mPa·s.

In another aspect, the present disclosure also provides a recyclable polyurethane system. The recyclable polyurethane system includes a reaction product made by reacting the polyol component having the structural Formula (I), or the polyol component having the structural Formula (II) or the polyol component having the structural Formula (III) and an isocyanate curing agent.

The reaction between a hydroxyl group of the polyol component having the structural Formula (I), the polyol component having the structural Formula (II) or the polyol component having the structural Formula (III) and a isocyanate group of the isocyanate curing agent results in formation of a carbamic acid ester or a urethane linkage.

In accordance with an embodiment, the isocyanates curing agent is selected from a group comprising of aliphatic diisocyanate and aromatic diisocyanate. Examples of the aliphatic diisocyanate curing agent include but are not limited to methylenebisphenyl isocyanates (MDI) hexamethylene diisocyanate (HDI), isophorone diisocyanate (IPDI) Examples of the aromatic curing agent include but are not limited to toluene diisocyanate (TDI), naphthalene diisocyanate (NDI), methylenebis-cyclohexyl isocyanate (HIVIDI), and tetramethylxylidene diisocyanate (TMXDI)).

In accordance with an embodiment, the polyol component having the structural Formula (I), or the polyol component having the structural Formula (II), or the polyol component having the structural Formula (III) and the isocyanate curing agent in the recyclable polyurethane system are added in a w/w ratio in a range of 0.1 to 15. In an example, the polyol component having the structural Formula (I) or the polyol resin component having the structural Formula (II) or the polyol component having the structural Formula (III) and the isocyanate curing agent in the recyclable polyurethane system are added in a w/w ratio in a range of 0.5 to 1.2. The ratio of the polyol component having the structural Formula (I), the polyol component having the structural Formula (II) or the polyol component having the structural Formula (III) and the isocyanate curing agent in the recyclable polyurethane system depends on the intended use and application of the polyurethane system.

In accordance with an embodiment, the recyclable polyurethane system may further comprise additives. Said additives may be added as a separate component in addition to the polyol component having the structural Formula (I), the polyol component having the structural Formula (II) or the polyol component having the structural Formula (III) and the isocyanate curing agent. In accordance with an embodiment, the total amount of additives in the recyclable polyurethane system does not exceed 80 wt. % of the total weight of the recyclable polyurethane system.

Additives include chain extenders, catalysts, surfactants, pigments, fillers, defoamers, wetting agents or combination thereof.

A chain extender is a reactive cross-linking agent that is used to modify the structure of the polyurethane synthesized by the reaction of the polyol component having the structural Formula (I), the polyol component having the structural Formula (II) or the polyol component having the structural Formula (III) and the isocyanate curing agent. In accordance with an embodiment, the chain extender is selected from a group comprising of aromatic diols, aliphatic diols and diamines. Examples of the chain extenders include but are not limited to ethylene glycol, propylene glycol, neopentyl glycol butanediol, ethanol amine, and diethyltriamine.

The selection of said additives is based on attributes or characteristics required in the recyclable polyurethane system and the end use or the intended application of the recyclable polyurethane system.

In accordance with an embodiment, the synthesis of the recyclable polyurethane system is a one step process. In an alternate embodiment, the synthesis of the recyclable polyurethane system is a two-step process. In the one step process, the polyol component having the structural Formula (I), or the polyol component having the structural Formula (II) or the polyol component having the structural Formula (III), the isocyanate curing agent and the chain extender are added together.

In the two-step process, in the first step, the polyol component having the structural Formula (I), or the polyol component having the structural Formula (II) or the polyol component having the structural Formula (III) is reacted with the isocyanate curing agent to form a prepolymer. In the second step of the two-step process, the prepolymer is converted into the final polyurethane by reacting with the chain extender.

In accordance with another aspect, the present disclosure also provides a process for preparing the polyol component having the structural Formula (I), and the polyol component having the structural Formula (II).

The process comprises reacting a compound having a structural Formula (IV) or a compound having a structural Formula (V) with water in the presence of a base at an elevated temperature to obtain a reaction mixture comprising the polyol component having the structural Formula (I) or a reaction mixture comprising the polyol component having the structural Formula (II) respectively.

In accordance with an embodiment, the reaction mixture comprising the polyol component having the structural Formula (I) or the polyol component having the structural Formula (II) is neutralized with an acid to a pH of 7. In accordance with an embodiment, the neutralization is done with a weak acid. Preferably, the weak acid is acetic acid, formic acid, oxalic acid etc.

In accordance with an embodiment, the reaction mixture comprising the polyol component having the structural Formula (I) or the reaction mixture comprising the polyol component having the structural Formula (II) is further treated with a solvent and water for separating a salt and the polyol component having the structural Formula (I) or the polyol component having the structural Formula (II). After separation of the salt and the polyol component having the structural Formula (I) or the polyol component having the structural Formula (II), the solvent and the water are removed by applying vacuum in a range of 10-60 mbar at a temperature in a range of 60 to 130° C. to obtain the polyol component having the structural Formula (I) and the polyol component having the structural Formula (II). Examples of the solvent include but is not limited to methyl isobutyl ketone, toluene, and xylene.

The polyol component having the structural Formula (I) and the polyol component having the structural Formula (II) is synthesized by an epoxide ring opening reaction of the compound having the structural Formula (IV) and the compound having the structural Formula (V) in the presence of water and base.

In accordance with an embodiment, the compound having the structural Formula (IV) is represented by:

$$\left( R_1 \right)_m \overset{A}{-} O \overset{B}{-} D \overset{}{-} \underset{X}{\triangleleft}_n$$ (Formula IV)

wherein
m=0 then n=4,
m=1 then n=3,
m=2 then n=2,
A is carbon or silicon
D is oxygen or nitrogen or carboxylic group,
X is oxygen,
$R_1$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.
B is independently selected from a group of arylene, alkylene-arylene, alkylene-arylene alkylene, alkenylene-arylene, alkenylene-arylene alkenylene, alkylene-arylene-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene In accordance with an embodiment, the compound having the Formula (IV) is selected from a group comprising of acetal glycidyl ethers, ketal glycidyl ethers, orthoesters glycidyl ethers and ortho carbonate glycidyl ethers. Examples of the compound having the Formula (IV) include but is not limited to 2,2'-(4,4'-(propane-2,2 diylbis(oxy))bis(methylene)bis(4,1-phenylene))bis(oxy)bis(methylene)dioxirane, 2,2'-(4,4'-(propane-2,2 diylbis(oxy))bis (methylene) bis(4,1-phenylene))bis(oxy) bis(methylene) glycidyl amines, bis(4-(oxiran-2-ylmethoxy)benzyloxy)methane, 2,2'-(4,4'-(ethane-1,1-diylbis(oxy))bis(methylene)bis(4,1-phenylene))bis(oxy) bis (methylene) dioxirane, and dimethylbis(4-(oxiran-2-ylmethoxy)benzyloxy)silane.

The base for the reaction of the compound having the structural Formula (IV) or the compound having the structural Formula (V) with water is selected from a group comprising of hydroxides of alkali metals and carbonates of alkali metals. Examples of the base include but are not limited to sodium hydroxide, potassium hydroxide, sodium carbonate, sodium bicarbonate, lithium hydroxide, barium hydroxide, calcium hydroxide, and magnesium hydroxide.

In accordance with an embodiment, the reaction of the compound having the structural Formula (IV) or the compound having the structural Formula (V) with water is carried out in a solvent. Examples of the solvent include but is not limited to toluene, xylene, methyl iso butyl ketone, acetone, methyl ethyl ketone, butyl cellosolve, ethers, and furans.

In accordance with an embodiment, the molar ratio of the compound having the structural Formula (IV) or the compound having the structural Formula (V) to water is in a range of 1:5 to 4:5.

In accordance with an embodiment, the reaction of the compound having the structural Formula (IV) or the compound having the structural Formula (V) with water is carried out at a temperature in a range of 60-120° C. to obtain the polyol component having the structural Formula (I) and the polyol component having the structural Formula (II).

The compound having the structural Formula (V) is represented by:

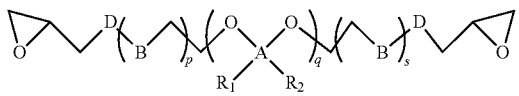

(Formula V)

wherein
A is carbon or silicon
D is oxygen or nitrogen or carboxylic group,
X is oxygen,
p, q, and s is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl.

B is independently selected from a group of arylene, alkylene-arylene, alkylene-arylene alkylene, alkenylene-arylene, alkenylene-arylene alkenylene, alkylene-arylene-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

In accordance with an embodiment, the compound having the Formula (V) is selected from a group comprising of poly ketals glycidyl ethers, and poly acetal glycidyl ethers. Examples of the compound having the Formula (V) include but are not limited to 1,4-bis((2-(4-oxiran-2-ylmethoxy)benzyloxy)propan-2-yloxy)propan-2-yloxy)methyl)benzene, 2-(4-((1-(4-(oxiran-2-ylmethoxy)benzyloxy)thyoxy)methyl)benzyloxy)ethoxy)methyl)phenoxy)oxirane, and 1,4-bis(((4-(oxiran-2-ylmethoxy)benzyloxy)methoxy) methyl)benzene.

The present disclosure also provides an alternate method of preparing the polyol component having the structural Formula (I), the polyol component having the structural Formula (II), and the polyol component having the structural Formula (III).

The process comprises of reacting a polyhydroxy compound having a structural Formula (VI) with a compound having a structural Formula (VII) or a compound having a structural Formula (VIII) or a compound having a structural Formula (IX) in the presence of an acidic catalyst to obtain the polyol component having the structural Formula (I), the polyol component having the structural Formula (II), and the polyol component having the structural Formula (III).

The polyol component (s) as obtained by this process is a mixture of a monomeric form of the polyol component having the structural Formula I, an oligomeric form of the polyol component having the structural Formula II and a cyclic acetal and cyclic ketal form of the polyol component having the structural Formula (III).

In the context of the present disclosure, the term "polyhydroxy" compound means comprising at least two or more hydroxyl group in the compound. The compound having the structural Formula (VI) is represented by:

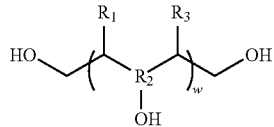

(Formula VI)

wherein w is 0 to 20

$R_1$, $R_2$, and $R_3$ is independently selected from a group of independently hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy.

In accordance with the compound having the structural Formula (VI) is selected from a group comprising of aliphatic polyhydroxy compound and the aromatic polyhydroxy compound. Example of the aliphatic polyhydroxy compound include but is not limited to ethylene glycol, polyethylene glycol, propylene glycol, poly propylene glycol, poly glycerol, sorbitol and pentaerythritol. Example of the aromatic polyhydroxy compound include but is not limited to bisphenol A, bisphenol F, bisphenol S, catechol, hydroquinone, and resorcinol.

The compound having the structural Formula (VII) is represented by:

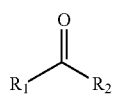

(Formula VII)

wherein $R_1$ and $R_2$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy.

In accordance with the compound having the structural Formula (VII) is selected from a group comprising of aliphatic aldehyde, aromatic aldehyde, aliphatic ketone, aromatic ketone. Examples of the aliphatic aldehyde include but is not limited to formaldehyde, paraformaldehyde, acetaldehyde, propionaldehyde, butyraldehyde etc. Examples of the aromatic aldehyde include but is not limited to benzaldehyde, 2 hydroxy benzaldehydes, 4 and hydroxybenzaldyhydes. Examples of the aliphatic ketone include but is not limited to acetone, methyl ethyl ketone, and methyl isobutyl ketone. Examples of the aromatic ketone include but is not limited to acetophenone, and benzophenone.

The compound having the structural Formula (VIII) is represented by:

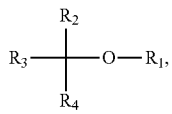

(Formula VIII)

wherein

R1 is independently selected from a group of hydrogen, alkyl, aryl, aralkyl, alkenyl, or alkynyl, $R_2$, $R_3$, $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy.

In accordance with the compound having the structural Formula (VIII) includes but is not limited to 2-methoxy propene, 2-2 dimethoxy propane, 2-ethoxy propene, 2-2 di-ethoxy propane, and 2-2 di-propoxy propane.

The compound having the structural Formula (IX) is represented by:

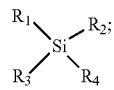

(Formula IX)

wherein $R_1$, $R_2$, $R_3$, $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy.

In accordance with an embodiment, the compound having the structural Formula (IX) includes but is not limited to tetra alkoxy silane, tri alkoxy silanes and di alkoxy silanes.

The acidic catalyst for the reaction of the polyhydroxy compound having the structural Formula (VI) with the compound having the structural Formula (VII) or the compound having the structural Formula (VIII) or the compound having the structural Formula (IX) is selected from a group comprising of a proton donor, a homogeneous acid catalyst or a heterogeneous acid catalyst. Example of the acidic catalyst include but is not limited to methane sulphonic acid, para toluene sulphonic acid, versatic acid, acetic acid, hydrochloric acid, sulphuric acid, phosphoric acid, acidic ion exchange resin, and sulphonates.

The solvent for the reaction of the polyhydroxy compound having the structural Formula (VI) with the compound having the structural Formula (VII) or the compound having the structural Formula (VIII) or the compound having the structural Formula (IX) is selected from a group comprising of dimethyl sulphoxide, dimethyl formamide, and dimethyl acetamide.

In accordance with an embodiment, the molar ratio of the polyhydroxy compound having the structural Formula (VI) to the compound having the structural Formula (VII), or the compound having the structural Formula (VIII), or the compound having the structural Formula (VII) is in a range of 1:5 to 7:5.

The reaction of the polyhydroxy compound having the structural Formula (VI) with the compound having the structural Formula (VII) or the compound having the structural Formula (VIII) or the compound having the structural Formula (IX) is carried out at a temperature in a range of 60-130° C.

In accordance with an aspect, a process for recycling the polyurethane system (PUs) that is a reaction product of the polyol component having the structural Formula (I), or the polyol component having the structural Formula (II) or the polyol component having the structural Formula (III) and the isocyanate curing agent is also disclosed. The process comprises of heating the polyurethane system (PUs) and immersing the heated polyurethane (PUs) system in an acid and a solvent to dissolve the polyol component(s).

In accordance with an embodiment, the polyurethane system (PUs) is heated to a temperature in a range of 80 to 220° C. In accordance with an embodiment, the heated polyurethane (PUs) system is immersed in the acid and the solvent for sufficient time period for the dissolution of the polyol component (s). The period that is required for dissolution of the polyol component (s) ranges from 2 to 24 hours.

In accordance with an embodiment, the acid in which the heated polyurethane system (PUs) is immersed is selected from a group comprising of a strong proton donor acid compound and a weak proton donor acid compound. The acid selection is done on the basis of time required for cleavage, temperature and the solvent used. Example of the acid includes but are not limited to methane sulphonic acid, para toluene sulphonic acid, versatic acid, acetic acid, hydrochloric acid, sulphuric acid, and phosphoric acid.

In accordance with an embodiment, the solvent is selected from a group comprising of aliphatic hydrocarbons, aromatic hydrocarbons, ethers, ketones, acetates, aldehydes, furans and water. Example of the solvent include but are not limited to toluene, xylene, methyl iso butyl ketone, acetone, methyl ethyl ketone, butyl cellosolve, ethers, furans, and alcohols.

The invention will now be described with respect to the following examples which do not limit the invention in any way and only exemplify the invention.

Example 1

Synthesis of re-workable polyol(s) 3,3'-(4,4'-(propane-2,2 diylbis(oxy))bis(methylene)bis(4,1-phenylene))bis(oxy)dipropane-1,2-diol

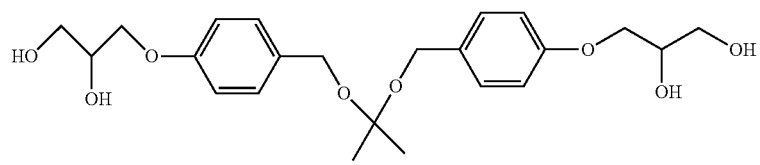 [SMILES: CC(C)(OCc1ccc(OCC(O)CO)cc1)OCc1ccc(OCC(O)CO)cc1]

50 gram of 2,2'-(4,4'-(propane-2,2 diylbis(oxy))bis(methylene)bis(4,1-phenylene))bis(oxy)bis(methylene)dioxirane was heated at 60° C. in the presence of 4 grams of water and 1 grams of 50% caustic soda (NaOH) for 1 hour to form a reaction mixture. The reaction mixture formed was then neutralized to get a pH of 7 by acetic acid. Further, methyl isobutyl ketone and water were added for separating salt and 3,3'-(4,4'-(propane-2,2 diylbis(oxy)) bis(methylene)bis(4,1-phenylene)) bis(oxy)dipropane-1,2-diol. After completing the hydrolysis reaction, the excess water and methyl isobutyl ketone were removed by applying 15 torr vacuum and at 110° C. to obtain 54 grams of 3,3'-(4,4'-(propane-2,2 diylbis(oxy))bis(methylene)bis(4,1-phenylene))bis(oxy)dipropane-1,2-diol.

Example 2

Synthesis of re-workable polyol(s) 4,4'-(propane-2,21-diylbis(oxy))bis(methylene)diphenol

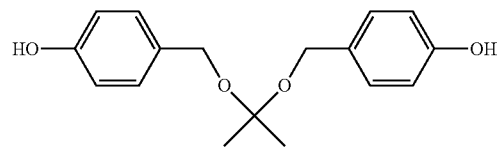 [SMILES: CC(C)(OCc1ccc(O)cc1)OCc1ccc(O)cc1]

Synthesis of 4,4'-(propane-2,2-diylbis(oxy))bis(methylene)diphenol was done by using 4-hydroxy methyl phenol (4HMP). 20 grams of 4-hydroxy methyl phenol (4HMP) was reacted with 7 grams of 2-methoxy propene in the presence of methane sulphonic acid and dimethyl sulphoxide. Further, 2-methoxy propene was added slowly at 18° C. in a controlled way. After the reaction was complete the solvents were vacuum stripped to obtain 25 gm of 4,4'-(propane-2,2-diylbis(oxy))bis(methylene)diphenol.

Example 3

Synthesis of re-workable polyol(s) 4,4'-(methylenebis(oxy)bis(methylene)) diphenol

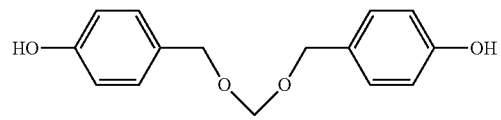 [SMILES: Oc1ccc(COCOCc2ccc(O)cc2)cc1]

Synthesis of 4,4'-(methylenebis(oxy)bis(methylene)) diphenol was done by using 4-hydroxy methyl phenol. 20 gm of 4-hydroxy methyl phenol 0.16 moles was reacted with 3 gm of paraformaldehyde in the presence of 60 gm methyl t-butyl ether and 0.2 gm of p-toluene sulphonic acid (pTSA). The reaction was carried at 50° C. temperature. After 1 hr, the temperature was increased to 55° C. and vacuum is applied for removing solvent. After the reaction was complete the solvent was vacuum stripped to obtain 22 gm of 4,4'-(methylenebis(oxy)bis(methylene)) diphenol.

Example 4

Synthesis of re-workable polyol(s) tetrakis(4-hydroxybenzyl) orthosilicates

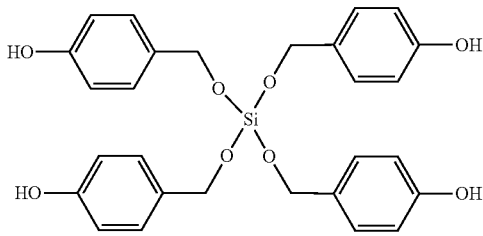 [SMILES: Oc1ccc(CO[Si](OCc2ccc(O)cc2)(OCc2ccc(O)cc2)OCc2ccc(O)cc2)cc1]

Synthesis of tetrakis(4-hydroxybenzyl) orthosilicate was carried out from 4-hydroxy methyl phenol. 20 gram of tetra methyl orthosilicate (0.13 moles) is heated with excess of 75 gram of 4-hydroxy methyl phenol with 0.2 gm of p-toluene sulphonic acid (pTSA). The reaction was maintained under nitrogen atmosphere at 120° C. temperature for reaction and removing methanol, then 100 mbar vacuum was applied to remove traces of methanol. After the completion of the reaction, 78-gram tetrakis(4-hydroxybenzyl) orthosilicates was obtained.

Example 5

Synthesis of re-workable polyol(s) 6,6,13,13-tetramethyl-5,7,12,14-tetraoxaoctadecane-1,18-diol

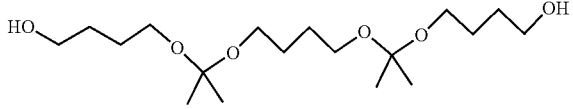 [SMILES: CC(C)(OCCCCO)OCCCCOC(C)(C)OCCCCO]

Synthesis of 6,6,13,13-tetramethyl-5,7,12,14-tetraoxaoctadecane-1,18-diol was done from 1,4 butanediol and 2 methoxy propene. 1,4 butanediol (0.11 moles) was reacted with 28 grams of 2 methoxy propene (0.38 moles) in the presence of 0.01 gram of p-toluene sulphonic acid and 40 gram of methyl isobutyl ketone. 2-methoxy propene was added slowly at 18° C. temperature in a controlled way and after 1 hr the temperature was increased to 50° C. for 3 hr. After that temperature was further increased to 100° C or 3 hr. After the completion of the reaction, vacuum was applied for removing solvent. At the end of reaction 19 gram of 6,6,13,13-tetramethyl-5,7,12,14-tetraoxaoctadecane-1,18-diol was obtained.

Example 6

Curing of Ketal Polyol with Isocyanates Agents 8 gram of 3,3'-(4,4'-(propane-2,2-diylbis(oxy))bis(methylene) bis(4,1-phenylene)) bis(oxy)dipropane-1,2-diol title product produced in example-1 was cured with 5.2 gm of methylenebisphenyl isocyanates(MDI). Curing was done at 80° C. for 2 hours and 100° C. for 2 hours in a closed system. Resultant polymeric material has glass transition temperature (Tg) of 68° C., tensile modulus of 2520 Pascal and flexural modulus of 3704 Pascal.

Example 7

Reworkability and Recyclability of Cured Polymer

Specimens (2 gm) of cured polymer in example 3° C. was kept in acidic solution (25% methane sulphonic acid wt/wt with water) and in presence of paraffin oil solvent at 160° C. temperature. Within an hour, the specimen started to soften and disintegrating in the acid solvent solution. Within 3 hours, the specimen was completely dissolved in the solution.

Specific Embodiments are Disclosed Below

A polyol component for a recyclable polyurethane system, the polyol component having a structural Formula (I) or a structural Formula (II) or a structural Formula (III):

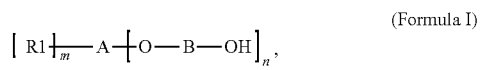
(Formula I)

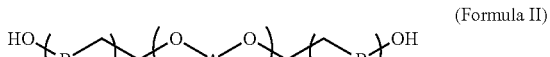
(Formula II)

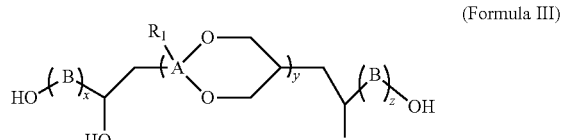
(Formula III)

wherein
m=0 then n=4,
m=1 then n=3,
m=2 then n=2,
A is carbon or silicon,
p, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

Such polyol component(s), wherein the polyol component having the structural Formula (I) are same as those mentioned in Table 1.

Such polyol component (s), wherein the polyol component having the structural Formula (II) are same as those mentioned in Table 2.

Such polyol component(s), wherein the polyol component having the structural Formula (III) are same as those mentioned in Table 3.

A process for preparing a polyol component having a structural Formula (I) and a polyol component having a structural Formula (II) for a polyurethane system. The process comprising reacting a compound having a structural Formula (IV) or a compound having a structural Formula (V) with water in the presence of a base at an elevated temperature to obtain a reaction mixture comprising the polyol component having the structural Formula (I) or a reaction mixture comprising the polyol component having the structural Formula (II), wherein
 the compound having the structural Formula (IV) and the compound having the structural Formula (V) is represented by:

$$\left(R_1\right)_m A\!-\!O\!\left(\!B\!\right)_p\!D\!\diagdown\!\!X\!\diagup\!\!\right)_n, \text{ and}$$
(Formula IV)

$$\diagdown\!\!\diagup\!\!O\!\left(B\right)_p\!\diagdown\!\!\left(\!O\!\diagdown\!A\!\diagup\!O\right)_q\!\diagdown\!\!\left(B\right)_s\!\diagup\!\!\diagdown\!\!O, \text{ respectively}$$
(Formula V)

wherein
m=0 then n=4,
m=1 then n=3,
m=2 then n=2,
A is carbon or silicon
D is oxygen or nitrogen or carboxylic group,
X is oxygen,
p, q, and s is independently from 1 to 20,
$R_1$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, alkylene-arylene, alkylene-arylene alkylene, alkenylene-arylene, alkenylene-arylene alkenylene, alkylene-arylene-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene, wherein the polyol component having the structural Formula (I) and the polyol component having the structural Formula (II) is:

$$[R1\!\!-\!\!\!\!{}_{m}\!\!A\!\!-\!\!\!\!{}_{}\!\!O\!\!-\!\!B\!\!-\!\!OH]_n,$$
(Formula I)

(Formula II)

$$HO\!\diagup\!\!\left(B\right)_p\!\diagdown\!\!\left(\!O\!\diagdown\!\!\!{}_{R_1}\!\!A\!\!{}_{R_2}\!\diagup\!O\right)_q\!\diagdown\!\!\left(B\right)_s\!\diagup\!OH$$

wherein
m=0 then n=4,
m=1 then n=3,
m=2 then n=2,
A is carbon or silicon,
p, q, and s is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-heteroalkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

Such process(es), wherein the compound having the structural Formula (IV) is selected from a group comprising of acetal glycidyl ethers, ketal glycidyl ethers, orthoesters glycidyl ethers and ortho carbonate glycidyl ethers.

Such process (es), wherein the compound having the structural Formula (V) is selected from a group comprising of poly ketals glycidyl ethers, and poly acetal glycidyl ethers.

Such process(es), wherein the molar ratio of the compound having the structural Formula IV or the compound having the structural Formula V to water is in a range of 1:5 to 4:5.

Such process(es), wherein the base is selected from a group comprising of hydroxides of alkali metals and carbonates of alkali metals.

A process for preparing a polyol component having a structural Formula (I), a polyol component having a structural Formula (II) and a polyol component having the structural Formula (III) for a polyurethane system. The process comprises reacting a polyhydroxy compound having a structural Formula (VI) with a compound having a structural Formula (VII) or a compound having a structural Formula (VIII) or a compound having a structural Formula (IX) in the presence of an acidic catalyst to obtain the polyol component having the structural Formula (I), the polyol component having the structural Formula (II) and the polyol component having the structural Formula (III), wherein the compound having the structural Formula (VI) is represented by:

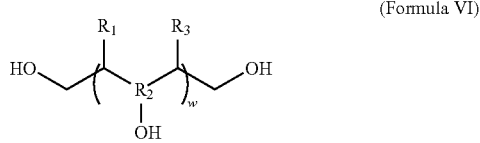

(Formula VI)

wherein w is 0 to 20

$R_1$, $R_2$, and $R_3$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, the compound having the structural Formula (VII) is represented by:

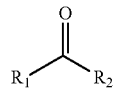

(Formula VII)

wherein $R_1$ and $R_2$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy.

the compound having the structural Formula VIII is represented by:

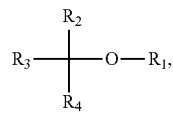

(Formula VIII)

wherein $R_1$ is independently selected from a group of hydrogen, alkyl, aryl, aralkyl, alkenyl, alkynyl;

$R_2$, $R_3$, and $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, the compound having the structural Formula (IX) is represented by:

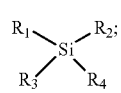

(Formula IX)

wherein $R_1$, $R_2$, $R_3$, and $R_4$ is independently selected from a group of hydrogen, alkyl, alkenyl, alkynyl, methylene, cycloalkyl, cycloalkenyl, cycloalkynyl, aryl, heterocyclic, heterocycloalkyl, cycloalkenyl, heteroaryl, alkoxy, alkoxyaryl, alkoxy alkyl, or aryloxy, wherein the polyol component having the structural Formula (I), the polyol component having the structural Formula II and the polyol component having the structural Formula (III) is:

(Formula I)

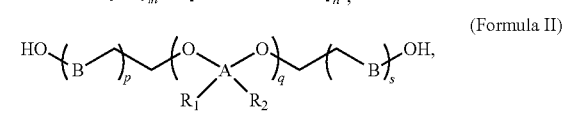

(Formula II)

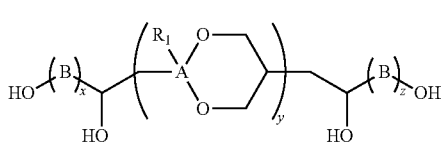
(Formula III)

wherein
m=0 then n=4,
m=1 then n=3,
m=2 then n=2,
A is carbon or silicon,
P, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene, alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-alkenylene, alkylene-heterocycloalkenylene-alkenylene, alkynylene heterocycloalkenylene, alkynylene-heterocycloalkenylene, or alkynylene.

Such process(es), wherein the polyhydroxy compound having the structural Formula (VI) is selected from a group comprising of aliphatic polyhydroxy compound and aromatic polyhydroxy compound having at least two hydroxyl groups.

Such process(es), wherein the compound having the structural Formula (VII) is selected from a group comprising of aliphatic aldehyde, aromatic aldehyde, aliphatic ketone, and aromatic ketone.

Such process(es), wherein the compound having the structural Formula (VIII) is selected from a group comprising of 2-methoxy propene, 2-2 dimethoxy propane, 2 ethoxy propene, 2-2 diethoxy-propane, and 2-2 dipropoxy-propane.

Such process(es), wherein the compound having the structural Formula (IX) is selected from a group comprising of tetra alkoxy silane, tri alkoxy silanes and di alkoxy silanes.

Such process(es), wherein the reaction of the polyhydroxy compound having the structural Formula (VI) with the compound having the structural Formula (VII) or the compound having the structural Formula VIII or the compound having the structural Formula (IX) is carried out at a temperature in a range of 60-130° C.

Such process(es), wherein the molar ratio of the polyhydroxy compound having the structural Formula VI to the compound having the structural Formula VII, the compound having the structural Formula VIII or the compound having the structural Formula VII is in a range of 1:5 to 7:5.

Such process(es), wherein the acidic catalyst is selected from a group comprising of proton donor, a homogeneous acid catalyst or a heterogeneous acid catalyst.

A recyclable polyurethane system comprising a reaction product made by reacting an isocyanate curing agent with a polyol component having a structural Formula (I), or a polyol component having a structural Formula (II) or a polyol component having a structural Formula (III); wherein the polyol component having the structural Formula (I) or the polyol component having the structural Formula (II) or the polyol having the structural Formula (III) is represented by:

(Formula I)

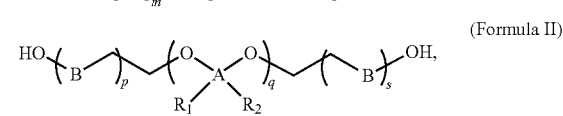
(Formula II)

(Formula III)

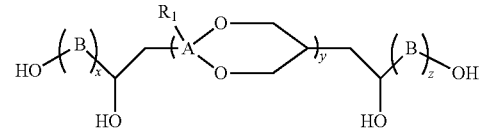

wherein
m=0 then n=4,
m=1 then n=3,
m=2 then n=2,
A is carbon or silicon,
P, q, s, x, y and z is independently from 1 to 20,
$R_1$ and $R_2$ is independently selected from a group of hydrogen, alkyl, alkenyl, alkynyl, cycloalkyl, cycloalkenyl, cycloalkynyl, aryl, heterocyclic, heterocycloalkyl, cycloalkenyl, heteroaryl, alkoxyaryl, or alkoxy alkyl,
B is independently selected from a group of arylene, arylene ethers, alkylene-arylene, alkylene-arylene, alkylene, alkenylene-arylene, alkenylene-arylene alkenylene, and alkylene-arylene.-alkenylene, alkynylene arylene, alkynylene-arylene-slkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene heteroarylene, alkynylene-heteroarylene-alkynylene, alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene alkylene, alkenylene-cycloalkylene, alkenylene cycloalkylene-alkenylene, alkylene-cycloalkylene alkenylene, alkynylene-cycloalkylene, alkynylene cycloalkylene-alkynylene, heterocycloalkylene, alkylene heterocycloalkylene, alkylene-heterocycloalkylene alkylene, alkenylene-heterocycloalkylene, alkenylene heterocycloalkylene-alkenylene, alkylene heterocycloalkylene-alkenylene, alkynylene heterocycloalkylene, alkynylene-heterocycloalkylene alkynylene, cycloalkenylene, alkylene-cycloalkenylene, alkylene-cycloalkenylene-alkylene, alkenylene-cycloalkenylene, alkenylene-cycloalkenylene-alkenylene, alkylene cycloalkenylene-alkenylene, alkynylene-cycloalkenylene, alkynylene-cycloalkenylene-alkynylene, heterocycloalkenylene, alkylene-heterocycloalkenylene, alkylene-hetero cycloalkenylene-alkylene, alkenylene-heterocycloalkenylene, alkenylene-heterocycloalkenylene-alkenylene, alkylene-heterocycloalkenylene-alkenylene, alkynylene heterocycloalkenylene, alkynylene-heterocycloalkenylene, or alkynylene.

Such recyclable polyurethane system, wherein the isocyanate curing agent is selected from a group comprising of methylenebisphenyl isocyanates (MDI), toluenediisocyanate (TDI), hexamethylene diisocyanate (HDI), naphthalenediisocyanate (NDI), methylenebis-cyclohexylisocyanate (HMDI) and isophorone diisocyanate (IPDI) and tetramethylxylidene diisocyanate (TMXDI).

A process for recycling a polyurethane system, the process comprising heating the polyurethane system and immersing the heated polyurethane system in an acid and a solvent at a temperature in a range of 80 to 220° C.; the recyclable polyurethane system being a reaction product of a polyol component having a structural Formula (I) or a polyol component having a structural Formula (II) or a polyol component having a structural Formula (III) and an isocyanate curing agent.

Such process (es), wherein the acid is selected from a group comprising of strong proton donor acid compounds and weak proton acid compounds.

Such process (es), wherein the solvent is selected from a group comprising of aliphatic hydrocarbons, aromatic hydrocarbons, ethers, ketones, acetates, aldehydes, furans, and water.

INDUSTRIAL APPLICABILITY

The polyol components(s) disclosed herein allows for the production of recyclable polyurethane (PUs) system having reworkable and recyclable properties. The recyclable and reworkable polyurethane component (s) disclosed herein offers several advantages which include excellent abrasion resistance, good electrical properties, excellent adhesions, low temperature flexibility and high strength.

The polyurethane system in accordance with the present disclosure have suitable characteristics that make them amenable for use in flexible and rigid foams, thermoplastic elastomers, surface coating, adhesives insulating sheets, electrical and electronics application. Polyurethane system of the present disclosure can be used as a matrix for the manufacturing of the high-performance recyclable composites reinforced with glass, carbon, polyaramid, and natural fibers. These composites are used in wind turbine rotor blades, automotive composites, sports and recreational goods, infrastructure, aerospace, defense and marine applications, consumer adhesives, industrial adhesives, structural adhesives, decorative coatings, industrial coatings, electrical, electronics, civil engineering and construction applications. These composite materials can also be recycled under specific conditions, leading to the separation and recovery of both the reinforcing fiber and the polyurethane polymer. These composite materials can be recycled precisely as the polyurethane matrix of the fabricated composite is derived from reworkable and recyclable polyol component(s).

We claim:

1. A polyol component for a recyclable polyurethane system, the polyol component having a structural Formula (I) represented by:

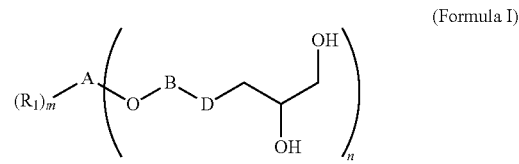

(Formula I)

wherein if m=0 then n=4, if m=1 then n=3, and if m=2 then n=2,

A is carbon,

D is oxygen or

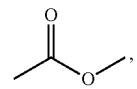

$R_1$ is independently hydrogen or alkyl and

B is independently arylene, alkylene-arylene, or arylene-alkylene-arylene.

2. The polyol component as claimed in claim 1, wherein the polyol component having the structural Formula (I) is selected from:

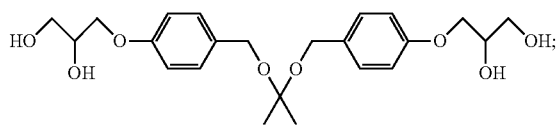

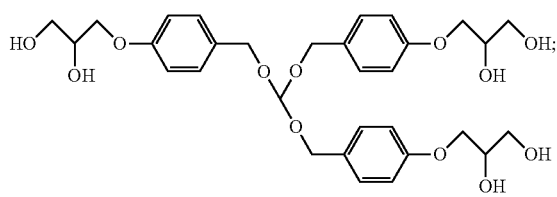 [SMILES: OCC(O)COc1ccc(COC(OCc2ccc(OCC(O)CO)cc2)OCc2ccc(OCC(O)CO)cc2)cc1]

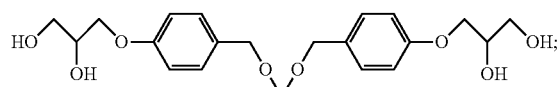
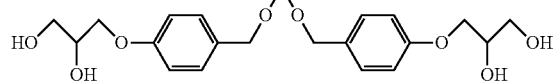
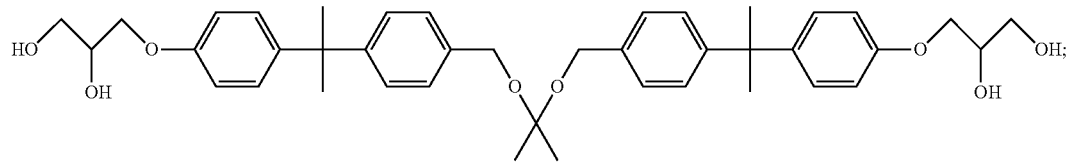 [SMILES: CC(C)(OCc1ccc(C(C)(C)c2ccc(OCC(O)CO)cc2)cc1)OCc1ccc(C(C)(C)c2ccc(OCC(O)CO)cc2)cc1]
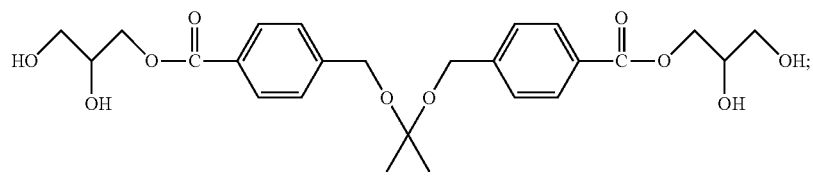 [SMILES: CC(C)(OCc1ccc(C(=O)OCC(O)CO)cc1)OCc1ccc(C(=O)OCC(O)CO)cc1]
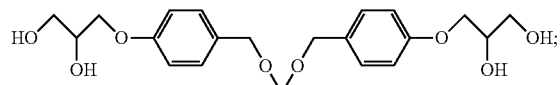
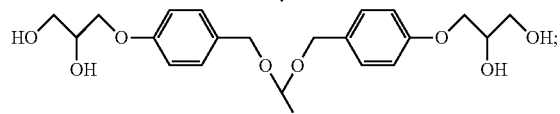
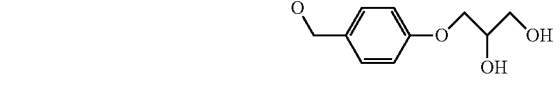
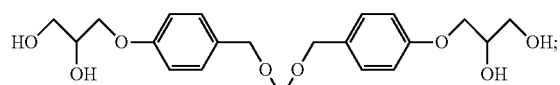
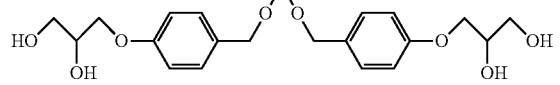
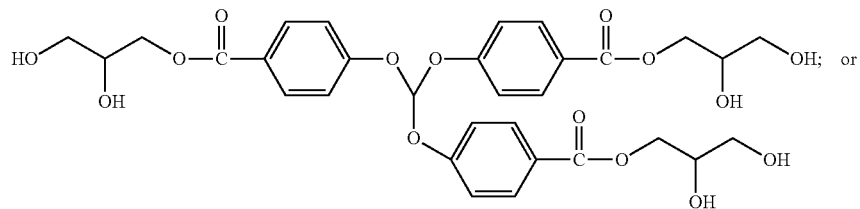

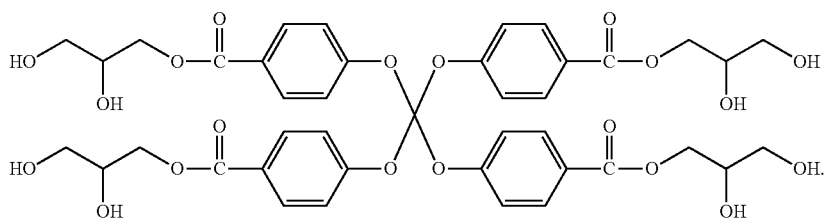 [SMILES: O=C(OCC(O)CO)c1ccc(OC(Oc2ccc(C(=O)OCC(O)CO)cc2)(Oc2ccc(C(=O)OCC(O)CO)cc2)Oc2ccc(C(=O)OCC(O)CO)cc2)cc1]

3. A process for preparing a polyol component having a structural Formula (I) for a polyurethane system, the process comprising:

reacting a compound having a structural Formula (IV) with water in the presence of a base at an elevated temperature to obtain the polyol component having the structural Formula (I)

wherein the compound having the structural Formula (IV) is represented by:

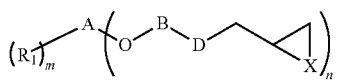   Formula (IV)

wherein if m=0 then n=4, if m=1 then n=3, and if m=2 then n=2,

A is carbon

D is oxygen or

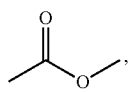

X is oxygen, $R_1$ is independently hydrogen or alkyl,

B is independently arylene, alkylene-arylene, or arylene-alkylene-arylene, wherein the polyol component having the structural Formula (I) is:

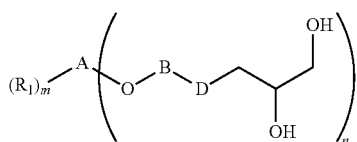   (Formula I)

wherein if m=0 then n=4, if m=1 then n=3, and if m=2 then n=2,

A is carbon,

D is oxygen or

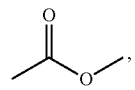

$R_1$ is independently hydrogen or alkyl, and

B is independently arylene, alkylene-arylene, or arylene-alkylene-arylene.

4. The process as claimed in claim 3, wherein the compound having the structural Formula (IV) is selected from a group consisting of ketal glycidyl ethers, orthoesters glycidyl ethers and ortho carbonate glycidyl ethers.

5. The process as claimed in claim 3, wherein the molar ratio of the compound having the structural Formula IV to water is in a range of 1:5 to 4:5.

6. The process as claimed in claim 3, wherein the base is selected from a group consisting of hydroxides of alkali metals and carbonates of alkali metals.

7. A recyclable polyurethane system comprising a reaction product made by reacting:

an isocyanate curing agent; with a polyol component having a structural Formula (I)

wherein the polyol component having the structural Formula (I) is represented by:

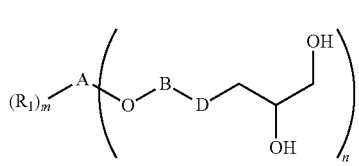   (Formula I)

wherein if m=0 then n=4, if m=1 then n=3, and if m=2 then n=2,

A is carbon,

D is oxygen or

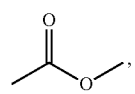

$R_1$ is independently hydrogen or alkyl,

B is independently arylene, alkylene-arylene, or arylene-alkylene-arylene.

8. The recyclable polyurethane system as claimed in claim 7, wherein the isocyanate curing agent is selected from a group consisting of methylenebisphenyl isocyanates (MDI), toluenediisocyanate (TDI), hexamethylene diisocyanate (HDI), naphthalenediisocyanate (NDI), methylenebis-cyclohexylisocyanate (HMDI) and isophorone diisocyanate (IPDI) and tetramethylxylidene diisocyanate (TMXDI).

* * * * *